United States Patent
Masson et al.

(10) Patent No.: US 8,860,943 B2
(45) Date of Patent: Oct. 14, 2014

(54) HIGH SENSITIVITY PLASMONIC STRUCTURES FOR USE IN SURFACE PLASMON RESONANCE SENSORS AND METHOD OF FABRICATION THEREOF

(75) Inventors: Jean-François Masson, Montreal (CA); Ludovic S. Live, Montreal (CA); Marie-Pier Murray-Méthot, Pierrefonds (CA)

(73) Assignee: Valorisation-Recherche, Limited Partnership, Montreal, QC ( * ) Notice: Subject to any disclaimer, the term of this patent is extended or adjusted under 35 U.S.C. 154(b) by 159 days.

(21) Appl. No.: 13/320,045

(22) PCT Filed: May 12, 2010

(86) PCT No.: PCT/CA2010/000730
§ 371 (c)(1),
(2), (4) Date: Jan. 10, 2012

(87) PCT Pub. No.: WO2010/130045
PCT Pub. Date: Nov. 18, 2010

(65) Prior Publication Data
US 2012/0105856 A1 May 3, 2012

Related U.S. Application Data

(60) Provisional application No. 61/213,151, filed on May 12, 2009, provisional application No. 61/272,686, filed on Oct. 21, 2009.

(51) Int. Cl.
G01N 21/55 (2014.01)
(52) U.S. Cl.
CPC .................................. G01N 21/554 (2013.01)
USPC ............. 356/445; 422/82.05; 438/27; 257/98
(58) Field of Classification Search
USPC .................. 356/445–448; 422/82.05; 438/27; 257/98
See application file for complete search history.

(56) References Cited

U.S. PATENT DOCUMENTS

| | | | |
|---|---|---|---|
| 7,501,649 | B2 | 3/2009 | Naya et al. |
| 2006/0197952 | A1 | 9/2006 | Chen et al. |
| 2006/0210425 | A1* | 9/2006 | Mirkarimi ...................... 422/56 |
| 2007/0286546 | A1 | 12/2007 | Masson et al. |
| 2008/0124565 | A1* | 5/2008 | Carlson et al. ................ 428/596 |
| 2008/0202926 | A1* | 8/2008 | Hontsu et al. ................. 204/400 |
| 2009/0040507 | A1 | 2/2009 | Van Wiggeren |
| 2009/0078153 | A1* | 3/2009 | Shchukin et al. .......... 106/14.44 |
| 2009/0134486 | A1* | 5/2009 | Fujikata ....................... 257/449 |
| 2009/0323060 | A1* | 12/2009 | Knipp ........................... 356/327 |
| 2011/0310383 | A1* | 12/2011 | Masson et al. ............... 356/319 |

* cited by examiner

Primary Examiner — Hoa Pham
(74) Attorney, Agent, or Firm — Norton Rose Fulbright Canada LLP; Alexandre Daoust

(57) ABSTRACT

There is disclosed a method for fabricating a plasmonic structure for use in a surface plasmon resonance sensor, comprising: coating a surface of an optically clear substrate with a monolayer of microspheres forming a sphere mask; etching the sphere mask to produce an array of microholes; depositing an adsorption layer on the etched sphere mask and the surface of the optically clear substrate; depositing a metallic film on the adsorption layer; and removing the sphere mask. This is also disclosed a plasmonic structure for use in a surface plasmon resonance sensor, comprising: an adsorption layer; and a metallic film deposited on the adsorption layer; wherein the adsorption layer and the metallic film comprises an array of microholes.

18 Claims, 16 Drawing Sheets

HIGH SENSITIVITY PLASMONIC STRUCTURES FOR USE IN SURFACE PLASMON RESONANCE SENSORS AND METHOD OF FABRICATION THEREOF

CROSS-REFERENCE TO RELATED APPLICATIONS

This application claims the benefits of U.S. provisional patent applications Nos. 61/213,151 and 61/272,686 filed on May 12, 2009, and Oct. 21, 2009, respectively, which are herein incorporated by reference.

TECHNICAL FIELD

The present invention generally relates to a high sensitivity plasmonic structure for use in a surface plasmon resonance sensor, and a method of fabrication thereof.

BACKGROUND

A technique for label-free detection of proteins resides on the use of surface plasmon resonance (SPR) biosensors. Proteins binding to an immobilized receptor on the SPR sensor results in small, albeit detectable change of refractive index due to the high sensitivity and resolution of SPR to refractive index. Proteins have a relatively large refractive index and are large molecules such that low detection limit in the nM or pM range can be achieved, without labeling the protein. However, SPR microbiosensors have yet to be developed and the optical properties of SPR-active metals, such as gold or silver, are not well characterized at the micrometer scale.

Also, exploitation of thin film SPR has nearly reached theoretical limits. The sensitivity of SPR instruments is identical to theoretical simulations, while the resolution is within the $10^{-7}$ RIU (refractive index unit) range.

However, there is still a need for an improved resolution of SPR instruments.

SUMMARY

According to one aspect of the present invention, there is provided a method for fabricating a plasmonic structure for use in a surface plasmon resonance sensor, comprising: coating a surface of an optically clear substrate with a monolayer of microspheres forming a sphere mask; etching the sphere mask to produce an array of microholes; depositing an adsorption layer on the etched sphere mask and the surface of the optically clear substrate; depositing a metallic film on the adsorption layer; and removing the sphere mask.

According to another aspect of the present invention, there is provided a plasmonic structure for use in a surface plasmon resonance sensor, comprising: an adsorption layer; and a metallic film deposited on the adsorption layer; wherein the adsorption layer and the metallic film comprises an array of microholes.

BRIEF DESCRIPTION OF THE DRAWINGS

Embodiments of the invention will be described by way of example only with reference to the accompanying drawings, in which.

DETAILED DESCRIPTION

Generally stated, the non-limitative illustrative embodiment described hereinafter relates to a high sensitivity plasmonic structure for use in a surface plasmon resonance (SPR) sensor, and a method of fabrication thereof. The plasmonic structure comprises an array of microholes defining triangles of 700 nm, 950 nm and 1.8 μm edge lengths, which transition to propagating SPR with microhole arrays of decreasing size. Such microhole arrays exhibit a short range SPR mode (as measured in the Kretschmann configuration SPR). Triangle arrays of different sizes and aspect ratio generally exhibit two absorption bands and a transmission maximum in the SPR spectrum. The maximum in transmission at approximately λ=600 nm exhibits the best analytical characteristics for triangle arrays. This maximum shifts significantly with increasing refractive index (RI) for the triangles of 950 nm and 1.8 μm edge lengths, with a sensitivity of 1993 and 1038 nm/RI respectively. This high sensitivity is comparable to the sensitivity of SPR sensors with smooth thin films with the same instrumental setup measured at 2971 nm/RI and much greater than with SPR sensors based on nanoparticles. Moreover, it was measured using the formation of a 16-mercaptohexadecanoic acid (MHA) monolayer that the penetration depth ($I_d$) of this peak is much lower at $I_d$=24 nm for the triangle arrays compared to $I_d$=230 nm for SPR on a smooth thin film. This short penetration depth makes this sensor template suitable for highly sensitive biosensing, as the peak bandwidth is relatively narrow, is less sensitive to bulk refractive than conventional SPR potentially reducing the effect of temperature drift, while improving the sensitivity to the detection of binding events. Microhole arrays are transitioning from a short range SPR behavior to a propagating SPR signal, similar to smooth Au thin films, but of higher RI sensitivity with the microhole arrays. The micron scale plasmonic structures exhibit interesting optical properties, which may be exploited in a biosensor format.

Surface Plasmon Resonance (SPR)

Figure 1:
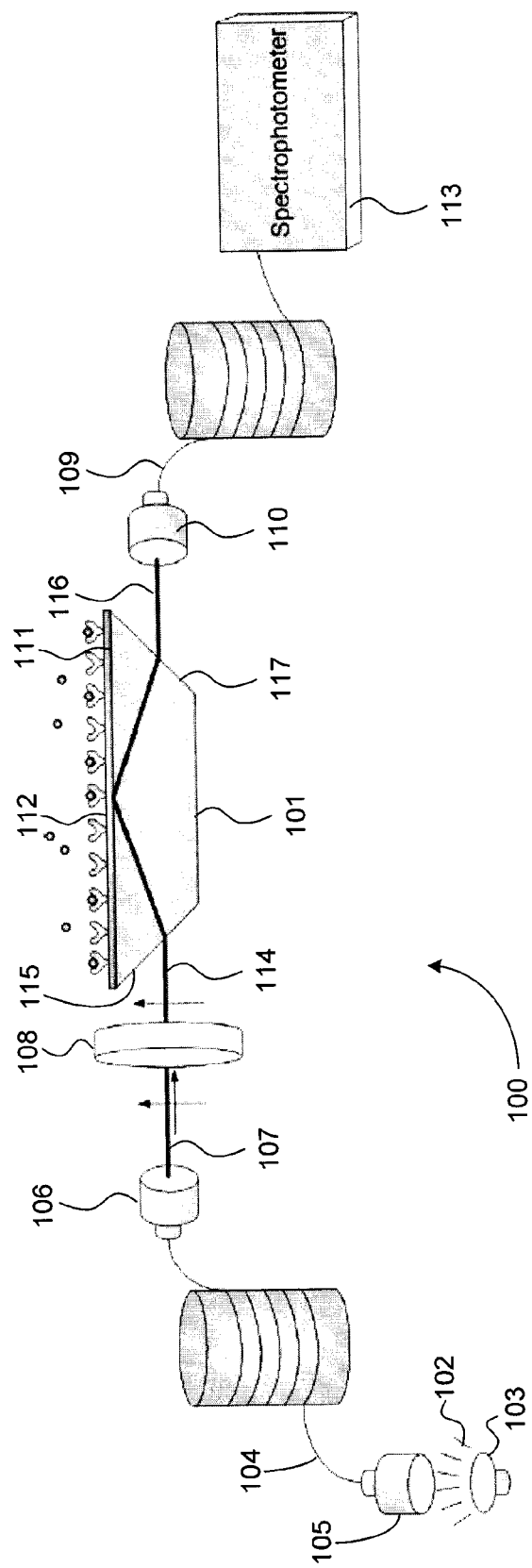
FIG. 1 is a schematic view of an example of a surface plasmon resonance (SPR) instrument using a dove prism.

Referring to FIG. 1, there is shown an illustrative example of a SPR instrument 100 in the Kretschmann configuration which is constructed based on a combination of wavelength-interrogation fiber optic SPR and total internal reflection in a BK7 dove prism 101. Broadband ligh 102 is produced from a halogen lamp 103 and is focused in a 200 μm-diameter visible and near infrared (Vis-NIR) fiber optic bundle (excitation fiber optic 104) using an inverted subminiature version A (SMA) collimating lens 105. Light exiting the excitation fiber optic 104 is collimated by a SMA collimating lens 106 into a beam 107 having to a diameter of about 3 mm. The collimated light beam 107 from the SMA collimating lens 106 is processed through a polarizer 108, propagates through the BK7 dove prism 101 and is collected with another 200 μm-diameter Vis-NIR fiber optic bundle (collection fiber optic 109) using an inverted SMA collimating lens 110. The collection fiber optic 109 can be identical to the excitation fiber optic 104. The BK7 dove prism 101 comprises a long face 111 to which is applied a SPR sensor 112.

The light exiting the collection fiber optic 109 is supplied to a spectrophotometer 113, for example a miniature spectrophotometer. Depending on the refractive index range to be covered, a short spectral range spectrophotometer (550 nm-850 nm) can be used to cover a RI range from 1.32 to 1.39 RIU (refractive index unit) or a longer spectral range spectrophotometer (550 nm-1100 nm) can be used to cover a RI range from 1.32 to 1.42 RIU.

To use a SPR imaging configuration, the collection fiber optic 109 is removed and replaced with a band pass filter (610±10 nm) (not shown). The collimated light exiting the band pass filter is then analyzed using a CCD camera such as provided by, for example, Andor technology (not shown). A 50:50 beam splitter can be mounted between the BK7 dove prism 101 and the band pass filter (not shown) for wavelength interrogation and imaging on a single platform.

The optical components 106, 108, 101 and 110 are aligned on a single optical axis. In fact, the above described SPR instrument 100 using a BK7 dove prism 101 defines a compact and a single axis optical path between the excitation fiber optic 104 and the collection fiber optic 109. Accordingly, there is no need for precise alignment of the optics at the angle of SPR excitation.

The collimated incident light beam 114 from the polarizer 108 impinges on the angular surface 115 of the BK7 dove prism 101 to propagate through the body of this prism at a single angle of 72.8° with respect to the vertical. At this angle, total internal reflection of the collimated light beam 114 occurs at the long face 111 of the BK7 dove prism 101. Also at this angle, surface plasmon on the SPR sensor 112 is excited at a wavelength of approximately 610 nm with aqueous solutions. With this configuration, the SPR instrument 100 combines multi-wavelength excitation with the spectrophotometer 113 to observe the SPR spectrum.

The active SPR area on the sensor 112 is <1 cm². This active SPR area can be made tunable by providing an iris (not shown) between the excitation fiber optic 104 and the BK7 dove prism 101.

The collimated light beam 116 exiting the angular surface 117 of the BK7 dove prism 101 and collected by the collection fiber optic 109 through the inverted SMA collimating lens 110 is analyzed by the spectrophotometer 113.

Surface Plasmon Resonance (SPR) Sensor 112

Figure 2:
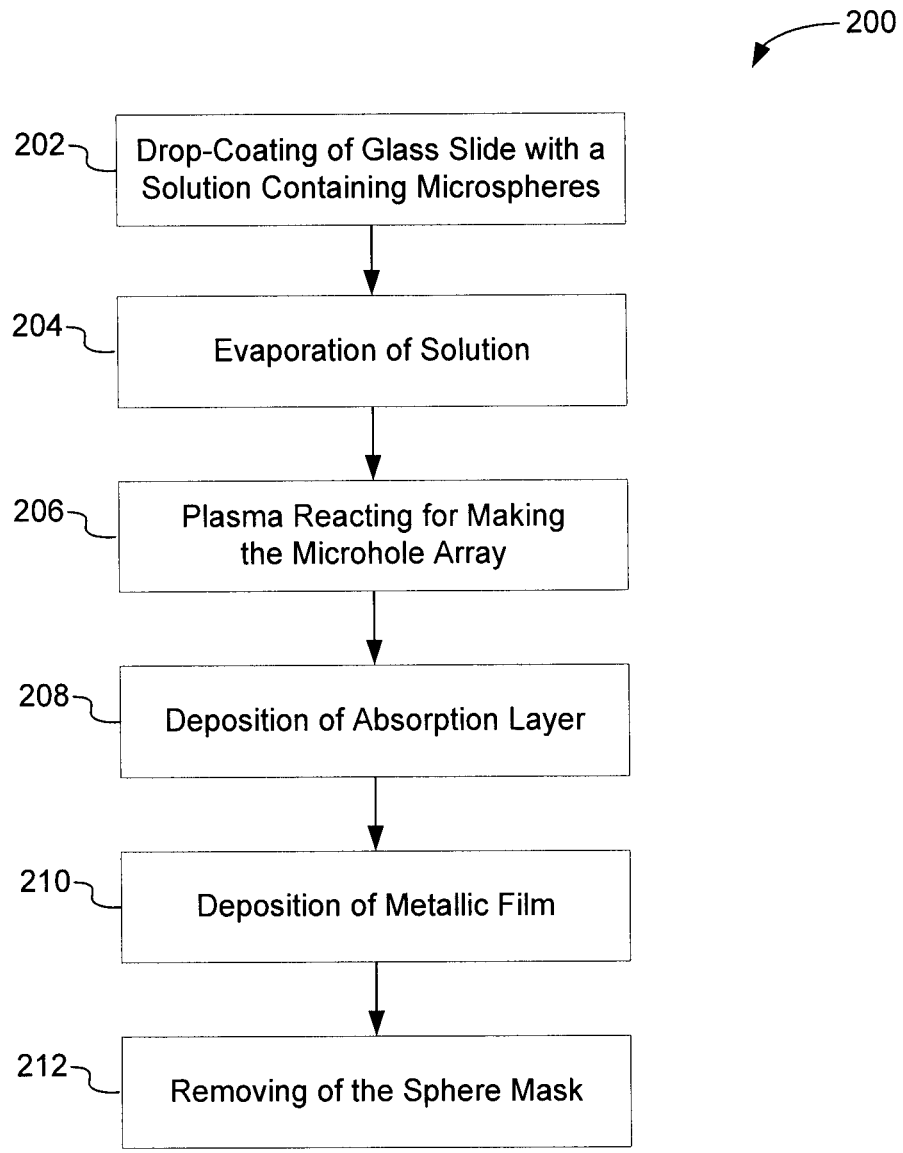
FIG. 2 is a flow diagram of a method of fabricating a SPR sensor.

Referring to FIG. 2, there is shown a flow diagram of a non-limitative example 200 of a method for fabricating a SPR sensor (SPR micro/nano sensor). The operations of the method 200 are indicated in blocks 202 to 212.

The method 200 starts with operation 202 where a solution (sphere solution) containing microspheres in suspension with a coefficient of variation <3-5% (depending on the size of the microspheres) and a concentration of microspheres of 10% by weight is drop-coated on a surface of a previously cleaned and dried optically clear substrate. As an alternative, drop-coating can be replaced by a Langmuir-Blodgett transfer of a well ordered monolayer of microspheres to the surface of the optically clear substrate. Other processes may also be contemplated as well to produce the monolayer of microspheres. Such drop-coating, Langmuir-Blodgett transfer or other process produces a well-ordered monolayer of microspheres that can be used as a mask (sphere mask).The substrate can be made of a slide of optically clear material such as, for example, glass, silica, silicon, plastic, polymer, indium tin oxide, etc.

In the case of drop-coating, the sphere solution may be acquired from, for example, Duke Scientific and is identified as Series 5000 (for example D5320A for a solution containing microspheres having a diameter of 3.2 µm). The above described solution containing latex microspheres can be used; however, microspheres of other polymer materials or microspheres of materials other than polymer but that can be etched can also be used. For example, 40 µL of the sphere solution may be used for a glass slide of 22×22 mm. With microspheres of 1.0 µm and 1.5 µm in diameter, 22 µL of the sphere solution may be mixed with 22 µL of 100% ethanol and 100 µL of ultrapure water to form the drop-coated solution. With microspheres of 3 µm in diameter, 30 µL of the sphere solution may be mixed with 30 µL of 100% ethanol and 100 µL of ultrapure water to form the drop-coated solution. The mixture is allowed to equilibrate at room temperature (approximately 10 minutes) before use. The size of the microspheres is not restrictive; for example, microspheres ranging from about 200 nm to 3 µm in diameter may be used.

In operation 204, the sphere solution is evaporated. In order to obtain a well-ordered monolayer of microspheres on the length scale from several hundreds of microns to the mm range, the evaporation of the sphere solution can be accomplished over a period from an hour to two hours. To reduce the rate of evaporation of solvent of the sphere solution, and eventually the ethanol and water of the above described mixture, such evaporation may take place, for example, under an upside down Petri dish, with the end of a 200 µL pipette tip lifting one end of the Petri dish to slow down evaporation. In this manner, large surface areas of approximately a few mm² of monolayer of microspheres with relatively few defects can be obtained.

In operation 206, a 30-minutes plasma etching in a plasma reactor, for example a Harrick PG-32, etches the sphere mask, more specifically the microspheres of the monolayer to define an array of microholes. Etch time controls the diameter of the microspheres and therefore of the microholes; etch times of less than 1 minute to more than 90 minutes have been employed but these boundaries are not restrictive. Microhole arrays having the same periodicity but of varying microhole sizes may be obtained by placing monolayers of microspheres in the plasma reactor at different locations such that the etch rate differs at each such location due to the presence of hot spots.

Then, in operation 208, a 0.5 nm to 5 nm thick Ti or Cr adsorption layer is deposited onto the etched microspheres of the monolayer and the surface of the optically clear substrate between the microspheres using, for example, a Cressington 308R sputter coater. The substrate, for example an optically clear slide comprising the monolayer may be mounted, for example, on two Petri dishes staked in the sputter coater chamber in order to increase the deposition rate. The base pressure in the chamber may be set <1×10⁻⁴ Pa, the sputtering pressure may be set at 1 Pa of Ar leak gas, and the power of the DC magnetron of the sputter coater chamber may be set at 50-100 W. Depositing Ti in these conditions results in a titanium oxynitride (TiOxNy) film comprising the array of microholes and observed from a dark gray metallic coloration. Alternatively, any other vapor phase metal deposition techniques, such as a metal evaporator or other deposition techniques using sputter coating can be used to deposit the Ti or Cr adsorption layer.

In operation 210, a metallic film, for example a Au or Ag film, is deposited onto the Ti or Cr adsorption layer using, for example, a Cressington 308R sputter coater to yield a Au or Ag film from 10 nm to 200 nm in thickness depending on the deposition time. Alternatively, any other vapor phase metal deposition techniques, such as a metal evaporator or other deposition techniques using sputter coating can be used to deposit the Au or Ag film. Also, successive layers of Au and Ag can be used as a metallic film. Moreover, copper, platinum, aluminum, palladium, etc. can eventually be used as the metallic film.

Finally, in operation 212, the sphere mask formed by the monolayer of microspheres along with the Ti or Cr adsorption layer and the Au or Ag metallic film on the microspheres may be removed by immersion in chloroform or other solvent, and using ultrasounds. A final wash with methanol or other solvent is performed to ensure that no residual material from the microspheres remains. An array of microholes defined by the microspheres of the monolayer then appears in the adsorption layer and the metallic film. To change of the properties of the plasmonic structure it is possible to deposit a further layer of Au, Ag or other metal on the metallic film to cover the surface of the optically clear substrate at the bottom of the microholes.

The resulting plasmonic structure for use in a SPR sensor comprises the above described adsorption layer deposited on the optically clear substrate, and the above described metallic film deposited on the adsorption layer, the adsorption layer and the metallic film comprising the array of microholes. When used as a SPR sensor, the non-metallized surface of the optically clear substrate (for example a slide) is applied to the long face 111 of the BK7 dove prism 101 through a refractive index matching oil having, for example, a Refractive Index (RI)=1.5150.

Characterization of the Triangles and Microhole Arrays

A mask formed of microspheres with a diameter of 1.0 µm produces, between the microholes of the array, triangles having a 700 nm edge length. Microspheres of 1.5 µm in diameter yield a triangle edge length of 950 nm, and triangles of 1.8 µm edge length are obtained with a mask formed of a monolayer of 3 µm microspheres. Triangles with edge lengths varying between 200 nm and 10-20 µm can be implemented. In the following description, the ratio of the edge length to the thickness of a triangle is defined as the aspect ratio of that triangle, as shown in Table 1 wherein $\lambda_{SPR}$ indicate the wavelength of the monitored SPR signal.

TABLE 1

| Triangles LSPR (Localized Surface Plasmon Resonance) signal | | | | | |
|---|---|---|---|---|---|
| 700 nm | | 950 nm | | 1.8 µm | |
| Aspect Ratio | $\lambda_{SPR}$ (nm) | Aspect Ratio | $\lambda_{SPR}$ (nm) | Aspect Ratio | $\lambda_{SPR}$ (nm) |
| 21 | 885 ± 7 | 17 | 1364 ± 11 | 21 | 2452 ± 3 |
| 23 | 902.2 ± 2.8 | 18 | 1319 ± 6 | 33 | 2477 ± 14 |
| 33 | 906.1 ± 3.4 | 34 | 1359 ± 4 | 41 | 2507 ± 7 |
| 41 | 908.9 ± 1.6 | 35 | 1355 ± 5 | 49 | 2546 ± 38 |
| 47 | 909.4 ± 2.2 | 53 | 1388 ± 8 | 95 | 2648 ± 17 |

Optical Properties of the Plasmonic Structure

Referring back to FIG. 1, at the above described prism propagation angle of 72.8°, wavelength interrogation of the optical properties from a metallic film micro-patterned with the microhole or triangle array was performed using a reflectance ratio between the P and S polarization of excitation light. A PI-Acton spectrophotometer with a triple grating tourette and an Andor CCD camera was used to monitor the SPR signal from 400 nm to 900 nm. A 150 gr/mm grating blazed at 500 nm was centered at 675 nm to accomplish this spectral window. Averaging an acquisition of 100 spectra with an integration time of 100 ms/acquisition resulted in a single measurement for each sample. Control experiments were performed using a blank glass slide and numerous Au films ranging from 10 nm to 50 nm thick with a 1 nm-thick Ti adsorption layer underneath the Au film and applied to the long face 111 of the BK7 dove prism 101. The reflectance ratio between the P- and S-polarization of excitation light was calculated using, for example, the Matlab software distributed by Mathworks, and the SPR wavelength was calculated using a minimum finding algorithm. This algorithm models the peak value using a second-order polynomial, where the zero of the derivative from the second-order polynomial results in the SPR wavelength.

Monolayer Formation

Using the method 200 of FIG. 2, a monolayer of MHA (16-Mercaptohexadecanoic Acid) was formed on an array of triangles of 1.8 μm edge length with an aspect ratio of 39. For that purpose, a 3.8 mM solution of MHA was prepared in ethanol and dissolved using ultrasounds. The formation of the monolayer of MHA was monitored using a fluidic cell having a volume of approximately 200 μL to minimize evaporation of the solvent. The array of triangles was placed into contact with ethanol for at least 15 minutes to equilibrate the SPR response. Thereafter, the SPR signal was monitored for 5 minutes in ethanol, followed by an exposition to the ethanolic MHA solution for 50 minutes and a final wash with ethanol for 5 minutes. A 1 mL volume was injected in a fluidic, flow cell to replace the prior solution with the solution to be monitored. Hence, the measurements were performed in a static solution. Continuous monitoring of the SPR signal during the monolayer formation allowed the measurement of the kinetic curve. The data were acquired at 1 Hz over the 1 hour-long experiment. The SPR response was converted to a kinetic curve (sensorgram) to measure the change in SPR response, from the beginning of formation of the monolayer of MHA to the final seconds of the MHA solution being in contact with the sample. The change in SPR wavelength was compared with a set of measurements obtained using a smooth gold film 50 nm thick with a Ti adsorption layer 2 nm thick. The measurements for the array of triangles were repeated four times and three measurements were acquired with the smooth gold film SPR.

Spectroscopy of Au Triangles in Transmission

Figure 3:
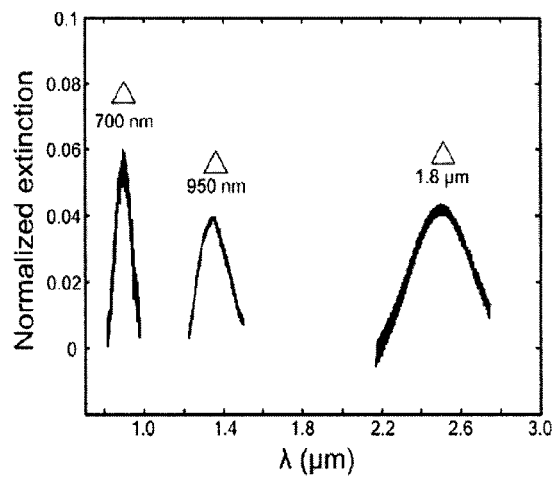
FIG. 3 is a graph showing extinction spectra that were measured in transmission spectroscopy for Au triangle arrays in air with various edge lengths.

The localized surface plasmon resonance (LSPR) signal from each array of Au triangles was measured in transmission spectroscopy. The arrays of Au triangles having edge lengths of 700 nm, 950 nm, and 1.8 μm are active in the near infrared (NIR) region, with significant differences in the excitation wavelength for each series of triangles (see FIG. 3). All samples were measured in air for comparison. Air does not absorb in the spectral region covered by the measurements, while most solvents would exhibit absorption in the NIR region. The 700 nm Au triangles have a strong absorption band near $\lambda=900$ nm, while the 950 nm Au triangles are showing an absorption peak near $\lambda=1.35$ μm and the 1.8 μm Au triangles have an absorption peak near $\lambda=2.5$ μm (see Table 1). As previously observed, these absorption peaks are also generally excited at longer wavelengths for larger aspect ratios, within the error on the measurement (n=3, one standard deviation reported as the error). Hence, it can be observed that LSPR is active in every Au triangle sample.

Figure 4:
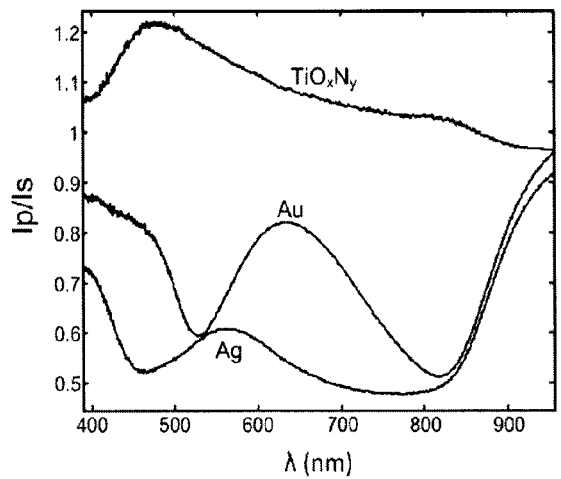
FIG. 4 is a graph showing SPR spectra for 1.8 µm triangles of different metal, Ag, Au, and TiOxNy with an aspect ratio of 36, 33, and 29, respectively.

Effect of the Metal on the Plasmonic Properties of 1.8 μm Triangles—SPR Measured in Total Internal Reflection Excitation of the arrays of Au triangles in total internal reflection with a SPR instrument in the Kretschmann configuration, such as SPR instrument 100 of FIG. 1, results in two peaks for the arrays of Au triangles with 1.8 μm edge length and an aspect ratio of 33 (see FIG. 4). Although many different Au structures of similar sizes have been reported as plasmon active, it is useful to investigate the properties of these arrays of triangles to confirm the plasmonic nature of the response observed. Sets of 1.8 μm edge length triangles were prepared with an approximate thickness of 50 nm, resulting in Au, Ag, and $TiO_xN_y$ triangles of aspect ratio of 33, 36, and 29 respectively. Au and Ag are plasmon active materials (negative real part of the dielectric constant) while $TiO_xN_y$ is SPR inactive due to a positive real part of the dielectric constant. As can be observed in FIG. 4, a similar SPR spectrum is obtained for 1.8 μm edge length Au and Ag triangles, while $TiO_xN_y$ triangles are SPR inactive. This result suggests that the optical response for Au and Ag triangles results from the surface plasmon.

Figure 5:
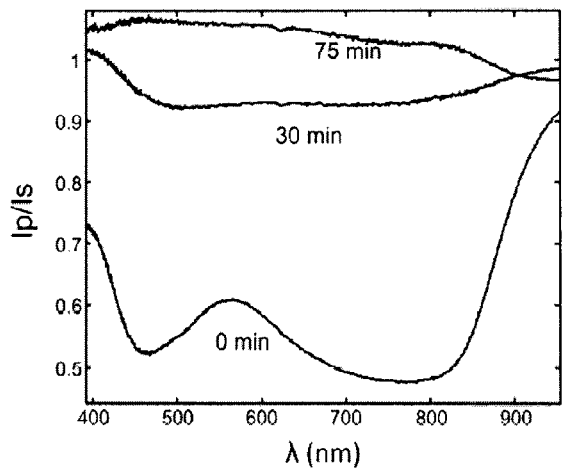
FIG. 5 is a graph showing SPR spectra for 1.8 µm Ag triangles (aspect ratio of 36) without oxidation (0 min), after 30 min and 75 min oxidation in an oxygen plasma.

To further confirm the plasmonic nature of the measured SPR response, the Ag triangles were oxidized in a plasma reactor filled with $O_2$. After 30 minutes of the $O_2$ treatment the surface of Ag triangles has partially oxidized, having a tarnished surface, and the SPR spectrum has greatly decreased (see FIG. 5). After 75 minutes of oxidation, the SPR response is null due to a full oxidation of the Ag triangle surface to $Ag_2O$ which can be observed by the black coloration of the film (typical for $Ag_2O$) compared to the characteristic metallic gray of Ag. Oxidation of the Ag triangles maintains the main physical characteristics of the triangle arrays (geometry, thickness, and periodicity) and forms a SPR inactive $Ag_2O$ thin film on the surface of the triangles. Hence, this experimentally confirms the plasmonic nature of the measured SPR response from 1.8 μm edge length Au and Ag triangles.

Figure 6:
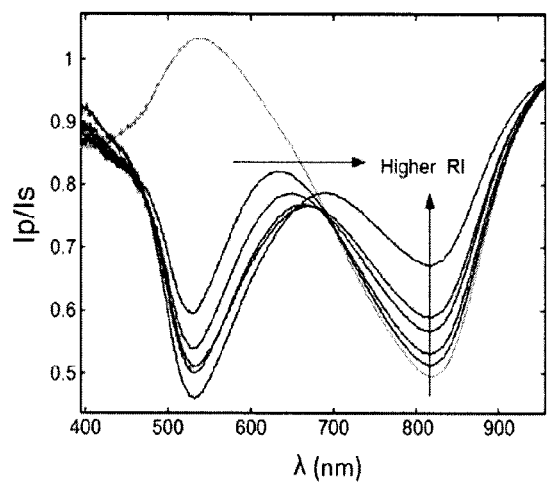
FIG. 6 is a graph showing the SPR spectrum for triangles of 1.8 µm with an aspect ratio of 33 measured with air (gray), RI=1.33359, RI=1.34722, RI=1.36320, RI=1.37335, and RI=1.39073 (black traces)

Edge Length and Aspect Ratio Influence on the Plasmonic Properties of Au Triangle Arrays Measured in SPR The SPR response of the Au triangles exhibited two distinct absorption peaks, observed at a wavelength of approximately $\lambda=525$ nm and 800 nm (see FIG. 6). The position of the peak at $\lambda=525$ nm is relatively invariable with geometrical aspects of the triangles, while the peak at $\lambda=800$ nm depends on the aspect ratio and the size of the triangles. The triangles with an edge length of 700 nm have an excitation wavelength of less than $\lambda=800$ nm, while the triangles with an edge length of 950 nm have an excitation wavelength of approximately $\lambda=805$ nm. The excitation wavelength is invariable relative to the aspect ratio of the triangles with an edge length of 700 nm and 950 nm within each series. For the triangles with an edge length of 1.8 μm, the excitation wavelength increases significantly from $\lambda=800$ nm to $\lambda=840$ nm for triangle arrays with the largest aspect ratio. Bulk refractive index sensitivity was also measured using sucrose solutions between RI=1.33 and RI=1.39. It was also observed with the multiple spectra acquired with different refractive index solutions that the peak at $\lambda=800$ nm is not very sensitive to refractive index (see FIG. 6).

There is a relatively large decrease in the intensity of the absorption peak at $\lambda=800$ nm for every triangle size and aspect ratio with increasing refractive index. Although it may be useful to exploit the absorbance-dependant property of refractive index calibration, it is not unusual when monitoring real-time processes in SPR with broadband light, as in the setup of FIG. 1, for example, to observe a drift of the absorbance intensity due to light source fluctuations. Thus, the use of the absorbance may be linked to a greater error in the measurement and poorer resolution of the measured response in the SPR sensorgram. This problem is also encountered in the measurement of the reflectivity in SPR imagers and results in lower resolution than for wavelength or angle scanning instruments.

Figure 7:
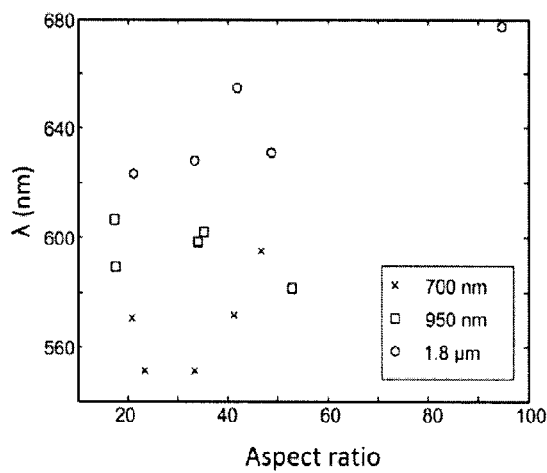
FIG. 7 is a graph showing the spectral position of the transmission maxima in water with various triangle edge lengths and aspect ratios.
Figure 8:
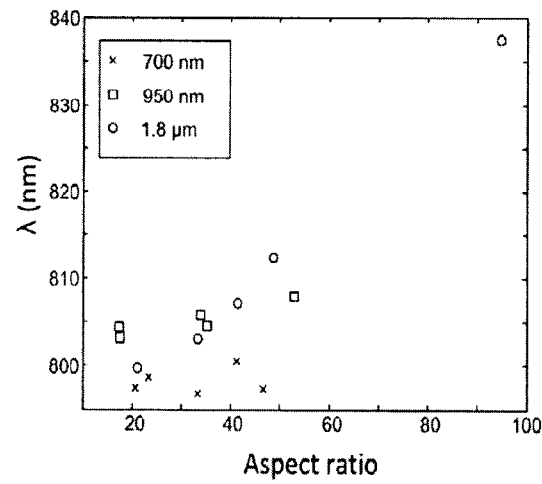
FIG. 8 is a graph showing the excitation wavelength for triangles with varying aspect ratios and edge lengths measured in total internal reflection with an air sample.
Figure 9:
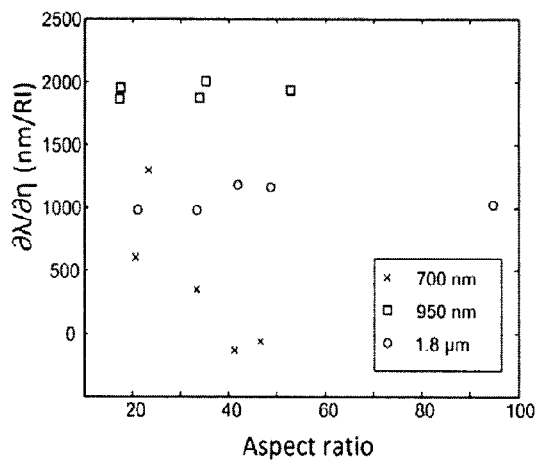
FIG. 9 is a graph showing the sensitivity to refractive index of the transmission maxima measured with aqueous sucrose solutions.
Figure 10A:
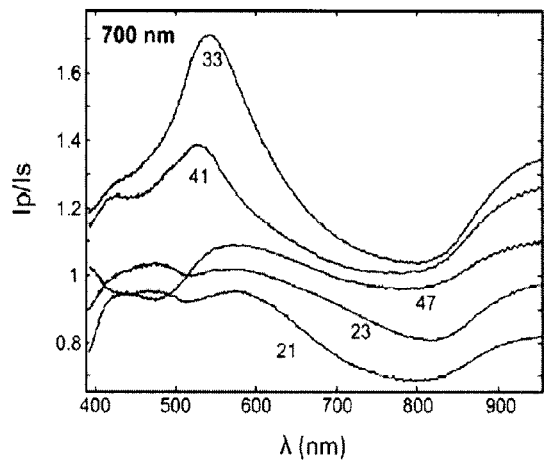
FIGS. 10*a* to 10*d* are graphs showing the SPR spectra in water of triangles with an edge length of 700 nm (FIG. 10*a*), 950 nm (FIGS. 10*b*), and 1.8 µm (FIG. 10*c*), with various aspect ratios, and the total internal reflection spectra for air (gray) and aqueous solutions of varying refractive indexes with a blank glass slide (FIG. 10*d*)
Figure 10B:
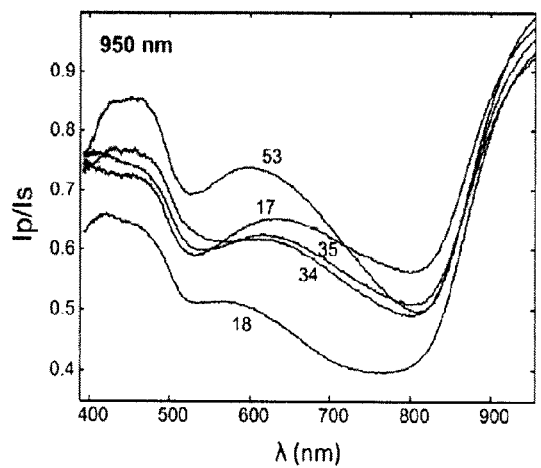
Figure 10C:
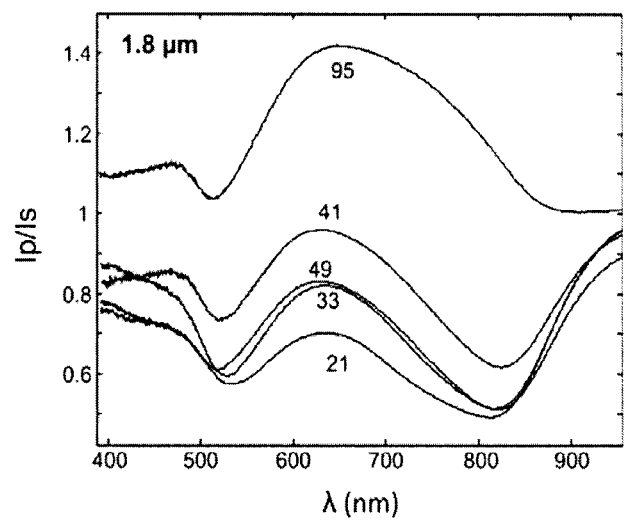
Figure 10D:
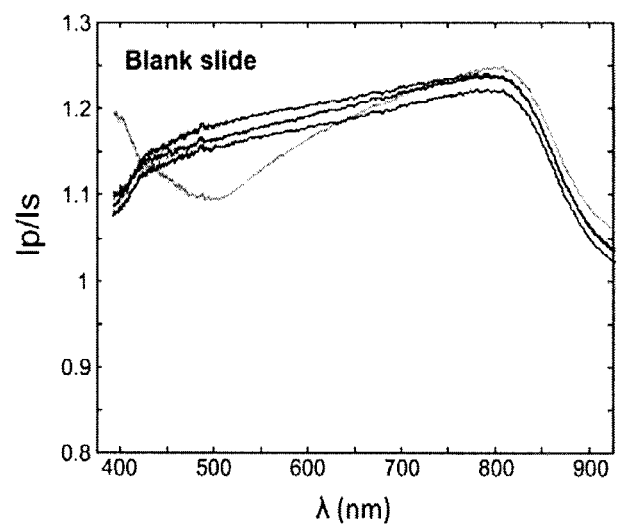
Figure 11A:
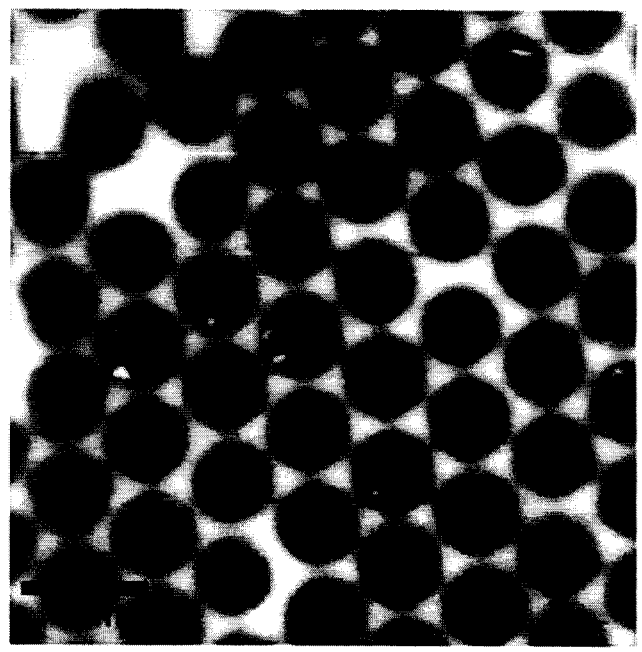
FIGS. 11*a* to 11*d* are graphs showing AFM images of microhole arrays with hole diameters of 2.5 (FIG. 11*a*), 2.2 (FIG. 11*b*), 2.0 (FIG. 11*c*), and 1.6 µm (FIG. 11*d*), and hole depth of between 60 and 70 nm, each AFM image corresponding to a 20×20 µm scan.
Figure 11B:
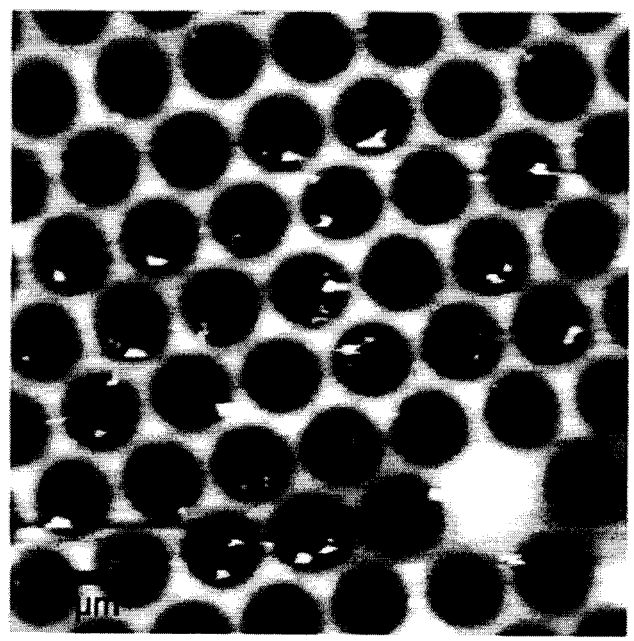
Figure 11C:
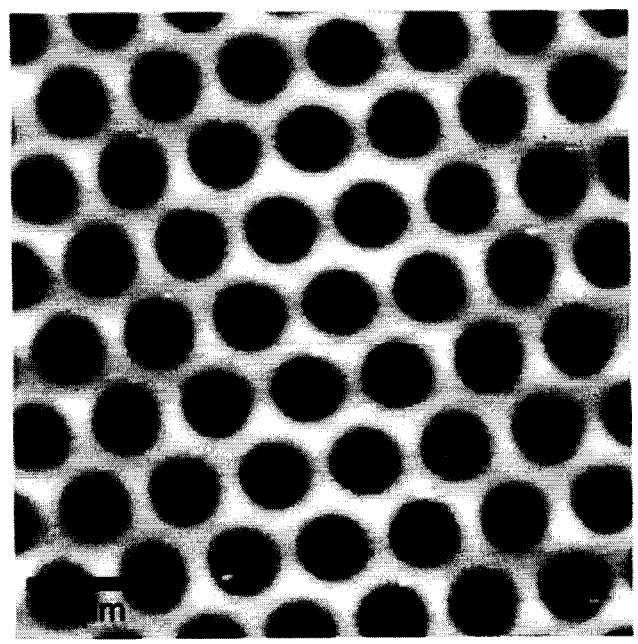
Figure 11D:
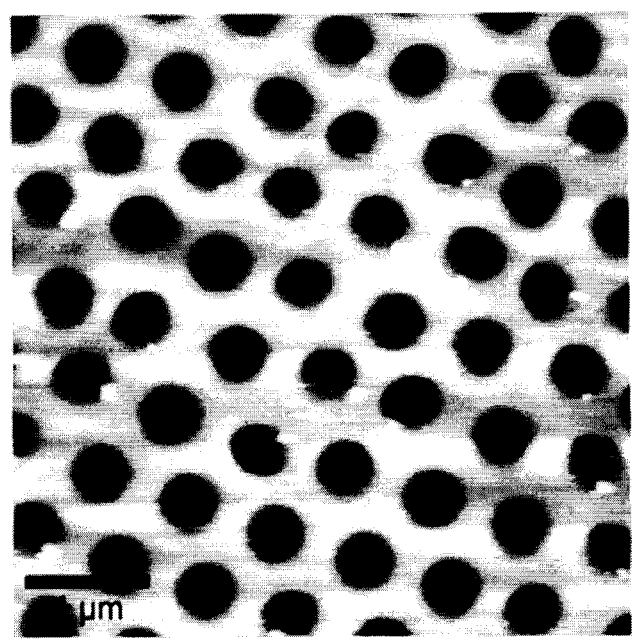

Wavelength and Sensitivity of the Maximum Transmittance of Au Triangles in SPR The SPR response of Au triangles shows a maximum transmission near λ=600 nm, between the absorption peaks at λ=525 and 800 nm, which significantly shifts in wavelength with increasing refractive index (see FIG. 6). Increasing the aspect ratio of the triangles with an edge length of 700 nm shifts the wavelength of the maximum in the SPR spectrum, resulting in a U-shape curve for increasing aspect ratio between λ=560 nm and 580 nm. Triangles with an edge length of 950 nm have a relatively invariable wavelength around λ=600 nm, while the peak position of the triangles with an edge length of 1.8 μm is increasing from λ=620 nm to 680 nm with increasing aspect ratio (see FIG. 7). Therefore, the sensitivity of this peak is much greater than the absorption peak at λ=800 nm ($\partial\lambda/\partial\eta$<100 nm/RIU, see FIG. 8). Triangles with an edge length of 950 nm are the most sensitive with an average sensitivity of 1993±374 nm/RIU. The error on the sensitivity represents two standard deviations on the mean sensitivity for each array of triangles with an edge length of 950 nm, as the sensitivity is constant with aspect ratio. The triangles with an edge length of 1.8 μm are less sensitive with 1038±96 nm/RIU. For the triangles with an edge length of 700 nm, the sensitivity varies greatly from nearly 0 nm/RIU to approximately 1000 nm/RIU with smaller aspect ratio (see FIG. 9). Thus, a significantly improved sensitivity is obtained by tracking the transmission maxima compared to the absorption peaks at λ=525 nm and 800 nm. The sensitivity is also greater than for nanoparticles (typically $\partial\lambda/\partial\eta$<500 nm/RIU) and is close to the sensitivity of conventional SPR in a same instrumental configuration ($\partial\lambda/\partial\eta$=2971 nm/RIU).

The SPR spectra for each triangle size and aspect ratio vary greatly in shape. FIGS. 10a to 10d show representative spectra acquired in water for each triangle size and aspect ratio. With triangles with an edge length of 700 nm (FIG. 10a), there is no absorption peak at λ=525 nm. However, a markedly increase in transmission is observed around λ=560 nm for aspect ratio 33 and 41, while the other spectra show a minor peak around λ=580 nm. The intensity variation for the peak at λ=560-580 nm follows the same U-shape in intensity as for the wavelength observed in FIG. 7. The absorption peak attributed to the short range SPR mode is observed in all cases at λ=800 nm for each sample, but the peak is very broad and of low intensity. For the triangles with an edge length of 950 nm (FIG. 10b), an absorption peak at λ=525 nm is observed, while the absorption peak at λ=800 nm is narrower especially for larger aspect ratios and of greater intensity comparatively to triangles with an edge length of 700 nm. Lastly, the triangles with an edge length of 1.8 μm (FIG. 10c) exhibited an absorption peak at λ=525 nm of greater intensity, while the peak at λ=800 nm is narrower and of the highest intensity among tested samples. One exception was observed with triangles having an aspect ratio of 95, which the absorption peak is unseen at λ=800 nm, but an anomalously increased transmission is observed. This was seen for every sample prepared with an aspect ratio of 95 with triangles having an edge length of 1.8 μm. As for FIG. 10d, it shows the total internal reflection spectra for air (gray) and aqueous solutions of varying refractive index with a blank glass slide.

Penetration Depth and Refractive Index Resolution for the Transmission Maxima Although the refractive index sensitivity is a useful measurement of the bulk refractive index changes, it does not indicate the penetration depth of the SPR sensing field. A film or nanostructure with a short sensing depth would exhibit a greater response to binding events occurring at the surface of the sensor than with another sensor of equal sensitivity with a greater penetration depth. This is usually the case when nanoparticle based LSPR is compared to conventional SPR. LSPR has a shorter penetration depth resulting in a larger signal for the formation of a monolayer than with conventional smooth film SPR.

To measure the penetration depth of the arrays of triangles, the formation of a MHA monolayer on the triangles with an edge length of 1.8 μm with an aspect ratio of 39 resulted in a change of SPR wavelength ($\Delta\lambda_{SPR}$) of 13±3 nm (n=4) from the formation of MHA monolayer during a period of 50 minutes. Comparatively, the formation of a MHA monolayer of smooth gold film resulted in $\Delta\lambda_{SPR}$=2.4±0.8 nm (n=3). The error on the measurement reflects two standard deviations on the mean SPR response. Using the equations from "Jung, L. S.; Campbell, C. T.; Chinowsky, T. M.; Mar, M. N.; Yee, S. S., *Langmuir* 1998, 14, 5636" for the thickness of an adsorbed layer, it is possible to calculate the penetration depth of the SPR mode in the arrays of triangles. Using the parameters for the refractive index of thiols ($RI_{SAM}$=1.45), the refractive index of ethanol ($RI_{solution}$=1.36), the sensitivity for a smooth gold film ($m_{Au}$=1765 nm/RI for the wavelength range of the experiment) and for the triangles ($m_{triangle}$=1038 nm/RI), and the penetration depth of SPR on a smooth film ($l_{d-Au}$=230 nm at λ=630 nm), one can obtain the penetration depth of the triangles ($l_{d-triangle}$) using Equations 1 to 3.

$$d = -\frac{l_d}{2}\ln\left(1 - \frac{\Delta\lambda_{SPR}}{m(RI_{SAM} - RI_{solution})}\right), \quad \text{Equation 1}$$

$$d_{Au} = d_{triangle}, \quad \text{Equation 2}$$

for MHA monolayer on both substrates, $$l_{d-triangle} = l_{d-Au}\frac{\ln\left(1 - \frac{\Delta\lambda_{SPR-Au}}{m_{Au}(RI_{SAM} - RI_{solution})}\right)}{\ln\left(1 - \frac{\Delta\lambda_{SPR-triangle}}{m_{triangle}(RI_{SAM} - RI_{solution})}\right)}, \quad \text{Equation 3}$$

where
d is the optical thickness of the monolayer for Au and the triangle arrays respectively.

Thus, using $\Delta\lambda_{SPR}$ for Au and the triangle arrays respectively, a value of 24 nm is obtained for the penetration depth of the triangles. This result is actually surprising for SPR excitation using total internal reflection, due to the relatively large penetration depth typically observed on Au films. However, this result is comparable to the 20 nm penetration depth observed in LSPR. Hence, the field of the short range SP mode observed here extends in the solution similarly to LSPR. This result is important for SPR biosensing due to a lesser sensitivity to bulk refractive index of the sensor with triangle arrays, causing a decreased influence of the temperature on the measurement. Since the temperature sensitivity to refractive index is constant, a sensor with smaller bulk refractive index sensitivity will have a smaller drift due to temperature compared to SPR sensors based on smooth films. Moreover, the signal from a binding event will be increased due to the short penetration depth. Lastly, the bandwidth at half height of the peak is approximately 150 nm, resulting in a relatively narrow peak and a refractive index resolution of $6\times10^{-5}$ RIU. However, this resolution was measured with low spectral resolution spectrophotometer (0.5 nm/pixel) to observe the full spectrum and could be significantly improved using better resolution spectrophotometer focused on the maximum transmission peak.

Transition from Triangles to Microhole Arrays Measured in SPR

In order to further understand the properties of the SPR mode present in plasmonic structures with a micrometer length scale, a series of samples were prepared to observe the optical properties in total internal reflection for the transition from triangle to microhole arrays. FIG. 11a to 11d show AFM (Atomic Force Microscopy) images of the microstructures ranging from triangle to microhole arrays. Three of the samples (FIGS. 11b to 11d) show a distinct microhole array aspect, while for the last sample (FIG. 11a), a triangle array was obtained with a slight overlap between adjacent triangles. For the triangle array, the microspheres were etched to a diameter of 2.5 μm (FIG. 11a), while the microhole arrays have a hole diameter 2.2 (FIG. 11b), 2.0 (FIGS. 11c), and 1.6 μm (FIG. 11d) for increasingly etched microspheres.

Figure 12:
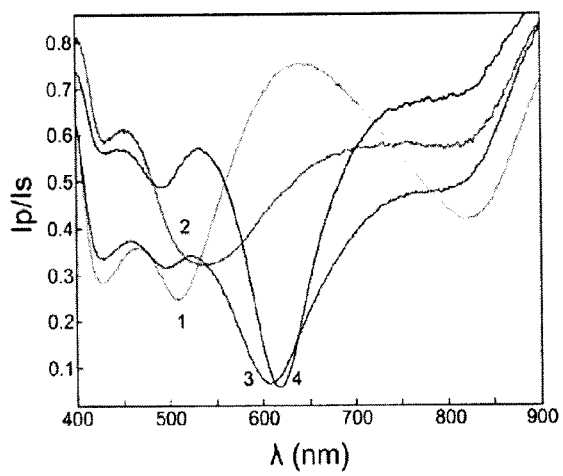
FIG. 12 is a graph showing the overlay of the SPR spectrum with microhole arrays acquired in water with increasing etching with a hole diameter for each sample being 2.5 µm (1), 2.2 µm (2), 2.0 µm (3), and 1.6 µm (4)

For the etched structure resulting in a triangle array (microsphere diameter of 2.5 μm after etching), the SPR response is similar to the other arrays of triangles with an edge length of 1.8 μm (see FIG. 12 with the hole diameter for each sample is being 2.5 μm (1), 2.2 μm (2), 2.0 μm (3), and 1.6 μm (4)) except for the presence of another strong absorption peak at around $\lambda=425$ nm. When the microhole diameter reaches approximately 2.2 μm, the width of the gold patch between holes is 0.8 μm wide by several tens of μm in length and is starting to optically respond as a propagating SPR response. A relatively broad SPR peak is appearing at $\lambda=541$ nm, which shifts to longer wavelength for an increased etch of the microspheres to $\lambda=608$ nm for microholes of 2.0 μm in diameter to reach $\lambda=618$ nm for the sample with the smallest holes of 1.6 μm in diameter.

Figure 13:
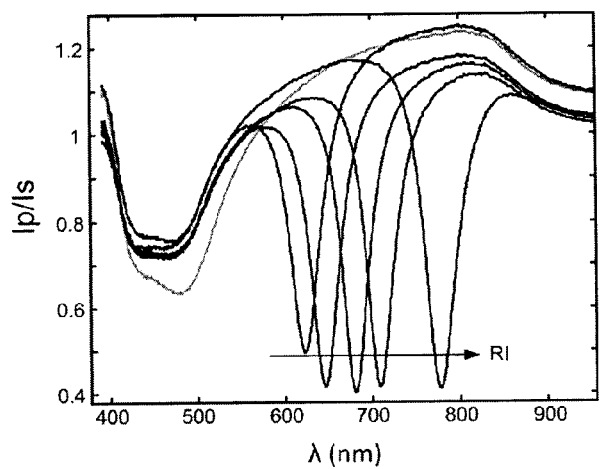
FIG. 13 is a graph showing the sensitivity to refractive index measured with sucrose solutions on a smooth Au film of 50 nm thin.
Figure 14A:
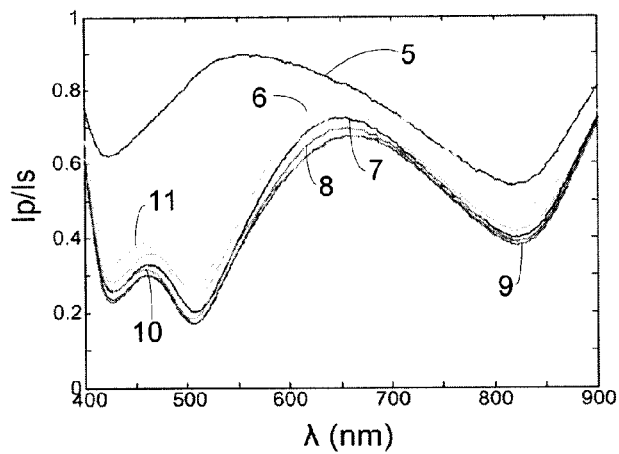
FIGS. 14*a* to 14*d* are graphs showing the SPR spectra of microhole arrays with a hole diameter of 2.5 µm (FIG. 14*a*), 2.2 µm (FIG. 14*b*), 2.0 µm (FIG. 14*c*) and 1.6 µm (FIG. 14*d*) measured with air (5) and sucrose solutions of RI=1.3333 (6), RI=1.3480 (7), RI=1.3554 (8), RI=1.3647 (9), RI=1.3755 (10), and RI=1.3888 (11)
Figure 14B:
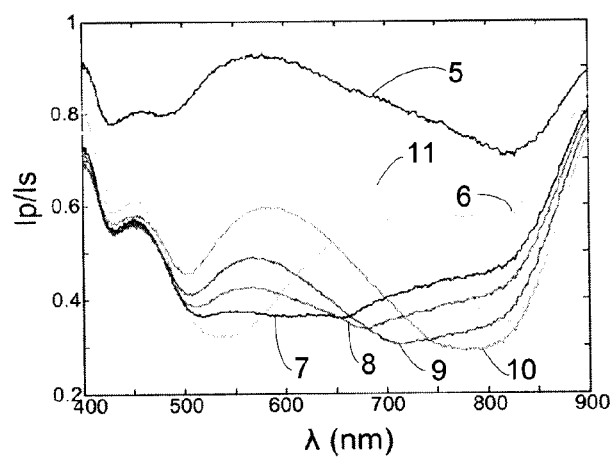
Figure 14C:
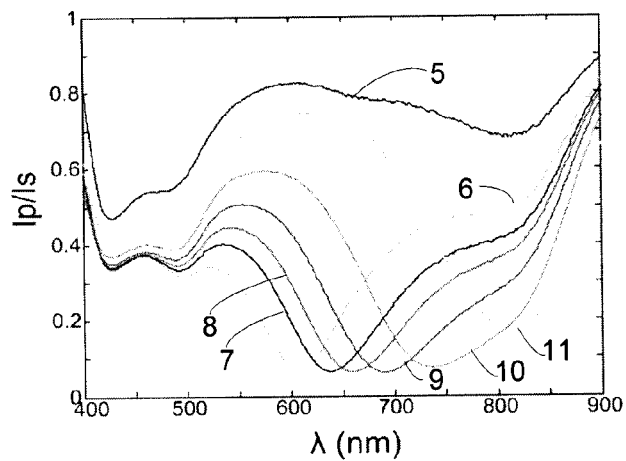
Figure 14D:
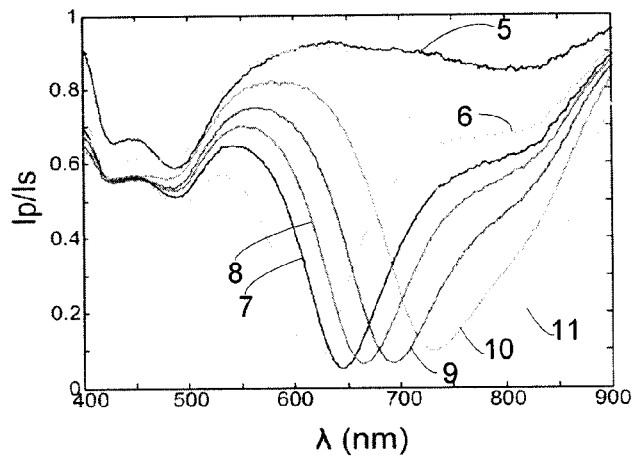

Furthermore, the width of the SPR peak and the excitation wavelength for the array of microholes with the smallest holes is very similar to the SPR signal from a 50 nm-thick Au film (see FIG. 13 which shows the sensitivity to refractive index measured with sucrose solutions on a smooth Au film 50 nm thick). Lastly, the intensity of the short range SPR peak at $\lambda=800$ nm is decreasing with smaller hole diameter. Thus, the increasing propagating SPR contribution in microholes of decreasing diameter is matched with a reduction in the short range SPR intensity. This confirms that the transition from the short range SPR mode to the propagating SPR occur with a coexistence of both SPR properties. This is similar to the conclusion reached previously for the transition from LSPR to short range SPR, where both the short range SPR and propagating SPR modes were active in sample of microstructures.

Sensitivity with Arrays of Microholes

Spectra for the calibration of the arrays of microholes are shown in FIGS. 14a to 14d. The triangle arrays (microspheres of 2.5 μm) exhibited a maximum transmission peak with a sensitivity of 315±30 nm/RIU (see FIG. 14a) which is about 3 times less sensitive than with the other triangles with an edge length of 1.8 μm (unetched samples). Increasing the etching of the microspheres (hole diameter of 2.2 μm) results in overlayed response of the propagating and short range SPR (see FIG. 14b). Thus, the sensitivity cannot be extrapolated with this microhole array. Further decreasing the hole size improves significantly the sensitivity, at 3700±400 nm/RIU and 3300±350 nm/RIU for the arrays of microholes having a diameter of 2.0 (FIGS. 14c) and 1.6 μm (FIG. 14d), respectively, within the RI range of 1.33-1.39. This sensitivity is greater than for SPR on a thin gold film, which exhibits a sensitivity of 2971±286 nm/RI within the same RI range (see FIG. 13). The propagating SPR peak is shaper and more intense with respectively a continuous Au film, microholes with a diameter of 2.0 and 1.6 μm.

Micro- and Nanohole Arrays Absorption Peak Sensitivity to Refractive Index

Figure 15:
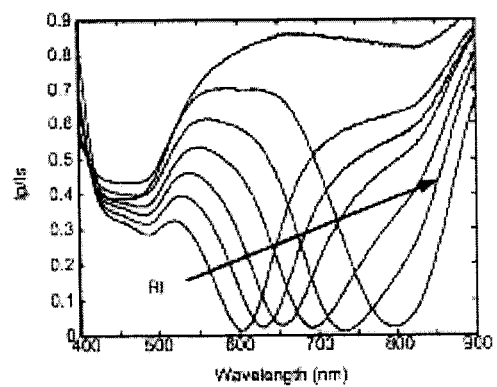
FIG. 15 is a graph showing the calibration of the SPR sensors with microhole arrays performed with sucrose solution of increasing refractive index for the spectrum going from left to right.
Figure 16:
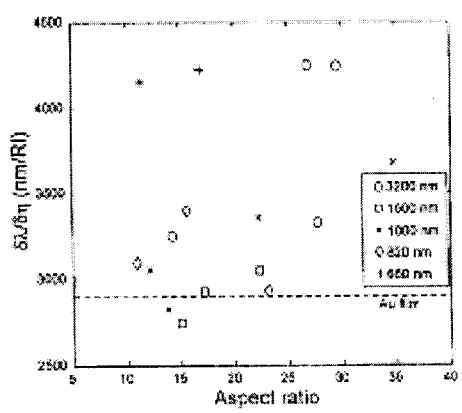
FIG. 16 is a graph showing the sensitivity of the SPR sensors with microhole arrays measured for fixed 50 nm hole arrays with diameter/periodicity from 0 to 0.6, the legend referring to the periodicity.

Referring to FIGS. 15 and 16, the size-depending sensitivity of fixed Au film 50 nm thick was investigated with various micro-nanohole arrays prepared by micro-nanosphere lithography technique with sphere diameters of 650 nm, 820 nm, 1.0 μm, 1.5 μm, and 3.2 μm. The diameter of each structure was controlled by different etch time prior the metallization. To describe the relation between the size of the triangle or hole, a parameter is introduced for fixed thickness: the hole/periodicity of the structure.

This parameter normalizes data for each periodicity and etch time. A diameter/periodicity=0 corresponds to a thin Au film, while a diameter/periodicity of 1 corresponds to unetched triangles. As observed in FIG. 15, the sensitivity is measured with glucose solutions and increasing RI causes a shift of the plasmonic band towards 900 nm. The intensity of the change in wavelength is measured as the sensitivity and reported in nm/RIU. A larger change corresponds to a more sensitive technique. As observed in FIG. 16, the microhole-array structures exhibit improved sensitivity compared to a thin film as used in conventional SPR sensors based on the Kretschmann configuration. This improvement can be as high as 4200 nm/RIU (improvement of 45%) for film prepared with microhole arrays of 650 nm periodicity. This is also observed for microhole arrays of 1.5 μm and 3.2 μm periodicity with diameter/periodicity of 0.5 to 0.6.

Shape of the SPR Band with Triangle and Hole Arrays

Figure 17:
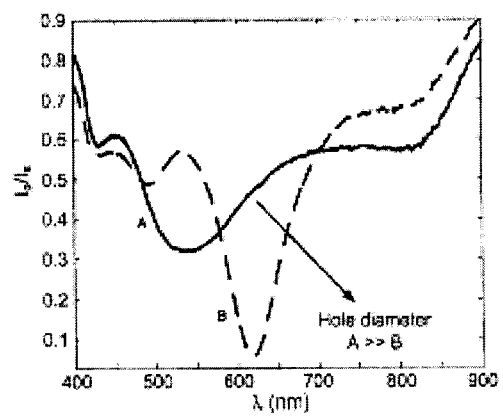
FIG. 17 is a graph showing the variation between the absorption band of microhole arrays of 0.5 (Curve A) and 0.1 (Curve B) diameter/periodicity ratio.
Figure 18:
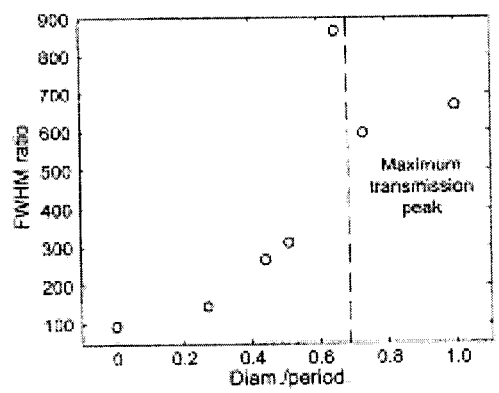
FIG. 18 is a graph showing the improvement of the FWHM ratio for diameter/periodicity tending towards 0.
Figure 19:
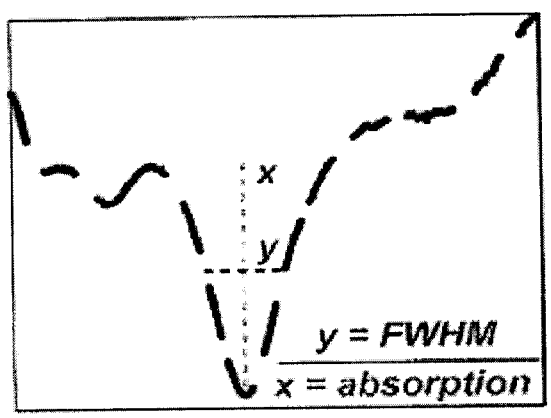
FIG. 19 is a graph showing the computations of the FWHM ratio.

Referring to FIGS. 17, 18 and 19, a narrow and intense SPR band improves resolution of the SPR measurements. Hence, a study to determine a ratio of the width to intensity (FWHM ratio) of the SPR band was undertaken for arrays of holes of 3.2 μm periodicity. FIG. 19 describes the methodology for obtaining the FWHM ratio. The SPR response for larger hole diameter (diameter/period of 0.5) is shown in FIG. 17 (Curve A), where it is observed that the absorption band around 525 nm is wide and yields to a FWHM ratio of nearly 400. This indicates that the peak is not only broad, but also of low intensity. A low value of FWHM ratio describes a narrow and intense SPR band. As observed in FIG. 18, the FWHM ratio decreases with decreasing diameter/periodicity ratio. This indicates that the resolution is better with film of smaller holes. FIG. 18 also shows that hole arrays with a diameter/periodicity ratio around 0.7 still gives a maximum transmission band like triangle structures.

Increasing the Thickness of the Au Film

Figure 20:
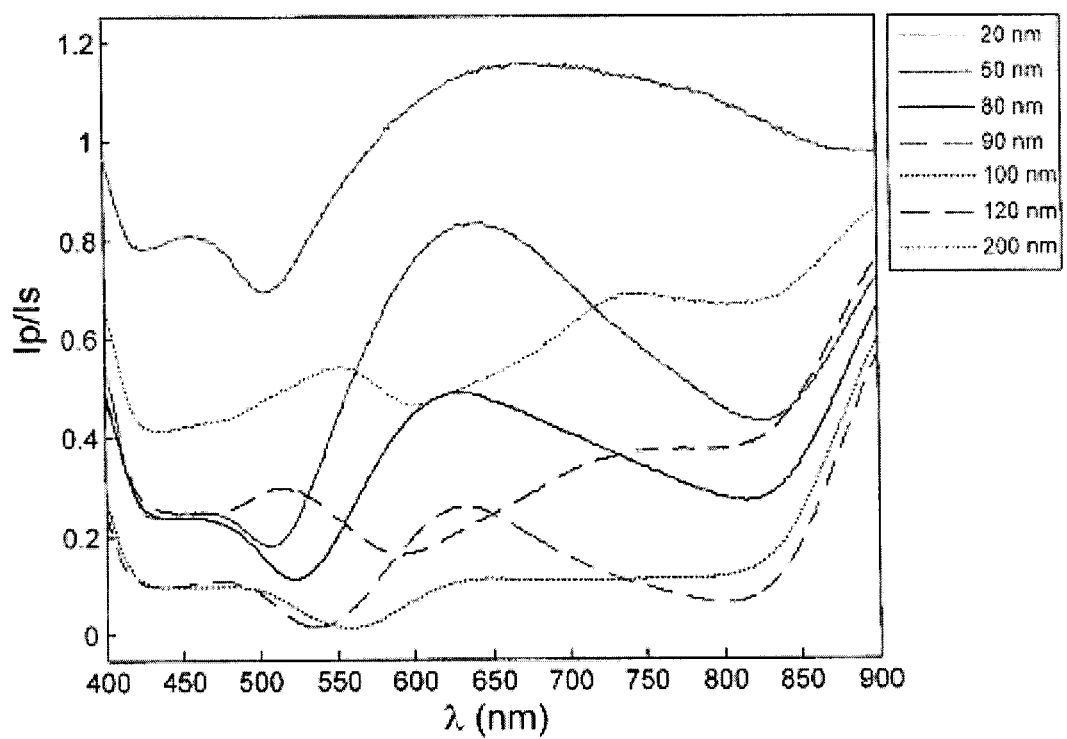
FIG. 20 is a graph showing the SPR spectrum with microhole arrays in water sample for hole arrays of 3.2 µm periodicity and 2.5 µm holes, the thickness varying from 20 nm to 200 nm, the legend referring to the thickness of the sample.
Figure 21:
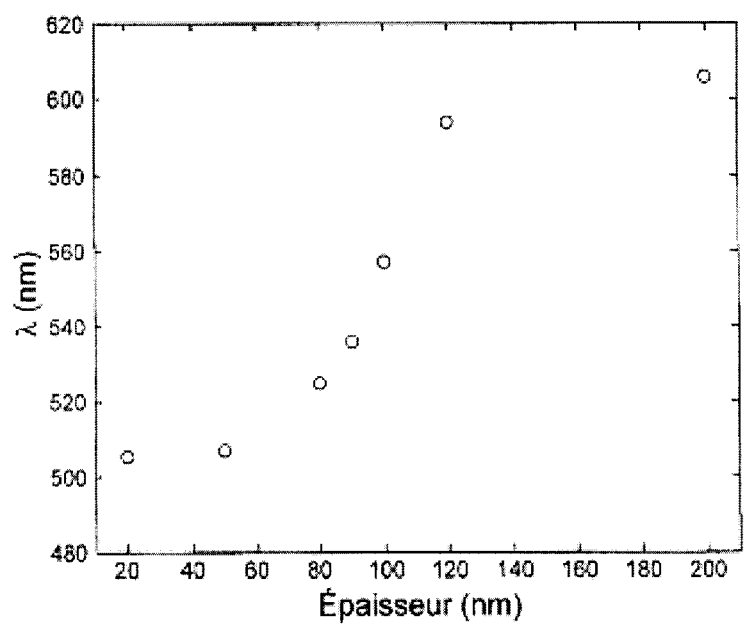
FIG. 21 is a graph showing the position of the SPR band in FIG. 20.

In order to observe the effect of the thickness of the metal film on the SPR properties, different microhole arrays of fixed 3.2 μm periodicity and of 2.5 μm diameter were prepared. It may be observed that the spectrum, as shown in FIG. 20 evolves as the thickness is increased for hole arrays. A first effect, as illustrated in FIG. 21, is the SPR band shifts progressively from 500 nm to 600 nm. Also, the intensity of the spectrum decreases from 10 nm to 100 nm, as illustrated in FIG. 20, with a secondary effect observed from 100 nm to 200 nm where the intensity of the spectrum increases. Conventional SPR effect is usually observed in film of 50 nm thick, but in this case, the SPR active thickness goes as high as 200 nm.

Figure 22:
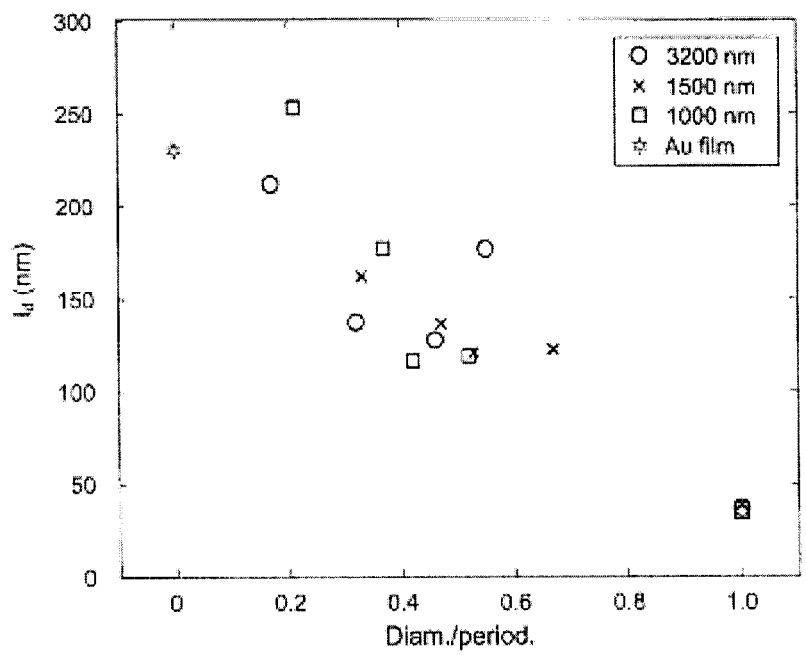
FIG. 22 is a graph showing the effect of the diameter/periodicity on the penetration depth of the SPR field, the legend referring to the periodicity.
Figure 23:
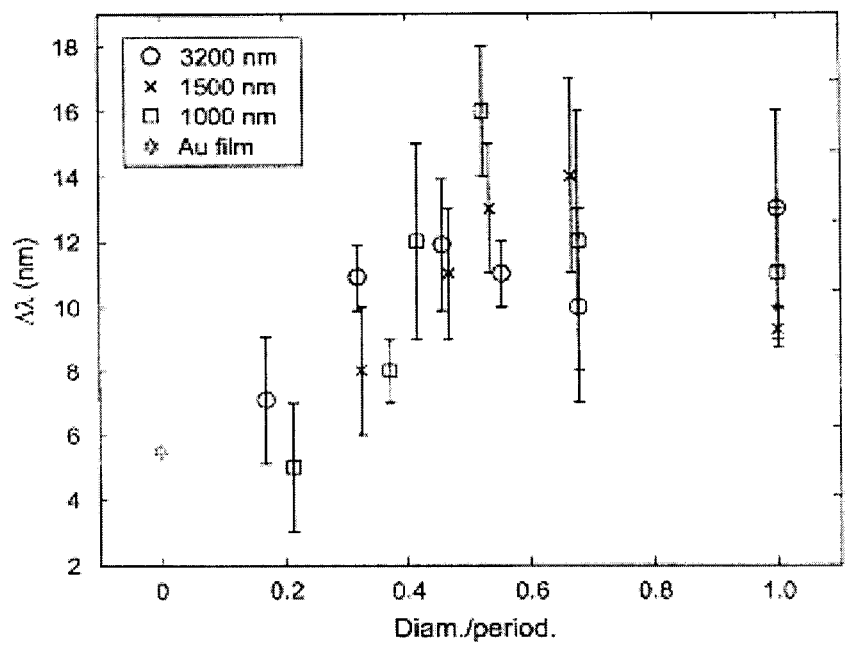
FIG. 23 is a graph showing the change of the SPR response to binding of 16-MHA, the legend referring to the periodicity.

Effect of the Formation of a Monolayer on the Micro Triangles and Microholes; Observation of the Penetration Depth and Intensity of the Response to a Monolayer FIGS. 22 and 23 illustrate the effect of the diameter/periodicity on the penetration depth ($l_d$). The penetration depth is a measure of the distance the electric field of SPR expands from the surface into the sensing medium. A short penetration depth is desired to monitor large changes of SPR response to binding of biomolecules, which will be further described below. Hence, as observed in FIG. 22, the penetration depth is linearly tunable from a thin film to triangles. It follows a linear trend with diameter/periodicity from approximately 250 nm for the thin Au film, to approximately 20 nm in triangles. This value was validated with various hole array structures of different periodicity and hole diameter. FIG. 23 shows the SPR response observed for the formation of a monolayer of MHA (16-mercaptohexadecanoic acid) over a period of 16 hours. The change in sensitivity to a monolayer improves by a factor of 2 with hole arrays of diameter/periodicity larger than 0.4 compared to thin Au film used in SPR sensors, for binding events occurring overnight. The improvement of sensitivity leads to improved response of biomolecules with the SPR sensor.

Sensitivity to the Detection of Biomolecules

Figure 24:
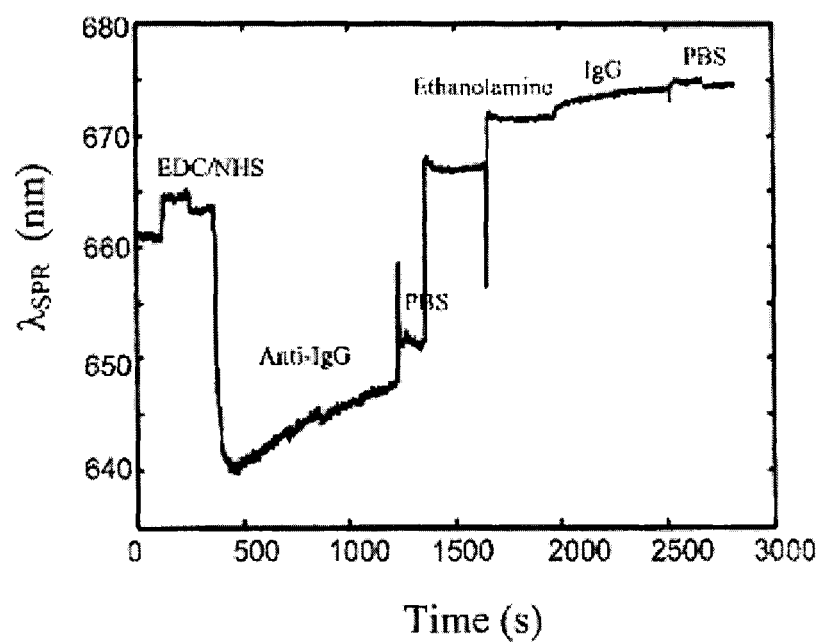
FIG. 24 is a graph showing the formation of a biosensor with a triangle array of 3.2 μm periodicity and diameter/periodicity of 1.
Figure 25:
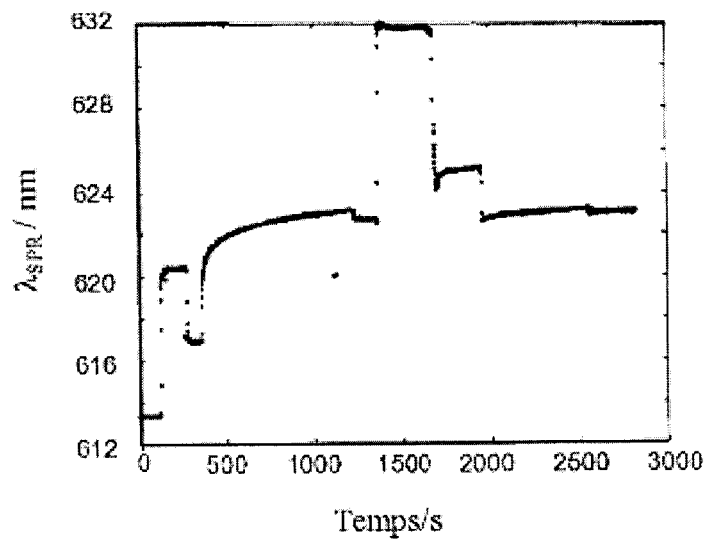
FIG. 25 is a graph showing the formation of a biosensor for IgG with a thin Au film used in conventional SPR.
Figure 26:
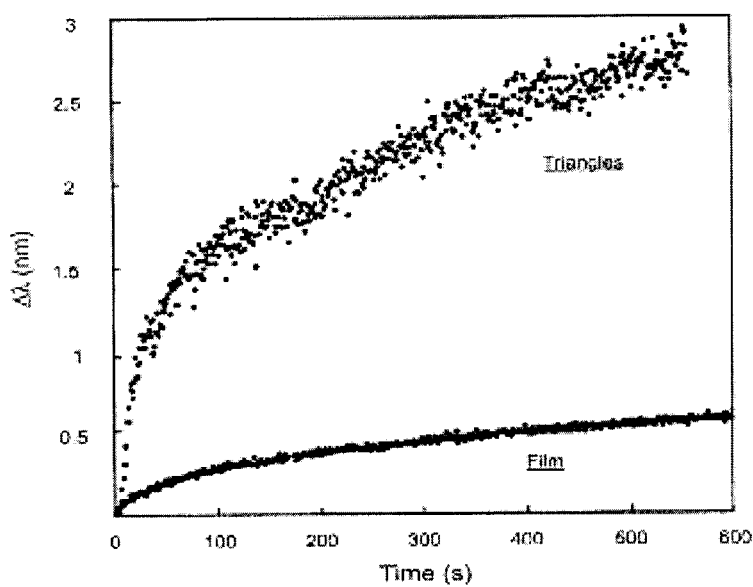
FIG. 26 is a graph showing an overlay of the responses from IgG at 10 nM with both triangle arrays (FIG. 24) and thin Au film (FIG. 25).

The formation of a biosensor was performed using a chemically or biologically selective layer binding to Au with a Au—S bond and a COOH group in the terminal position of the monolayer to detect corresponding molecules. The COOH group is activated with EDC-NHS chemistry followed by immobilization of anti-IgG. The unreacted sites are capped with ethanolamine and the sensor is exposed to PBS to stabilize the biosensor. Thereafter, the sensor is exposed to a biomolecule, IgG (immunoglobulin Gamma) at a concentration of 10 nM and binds to the SPR sensors causing a change in the response measured. This is the physical principle on which SPR biosensor is based. This was performed for a triangle array (FIG. 24) and a thin film (FIG. 25). It is observed that the SPR response for triangle arrays yields a larger response in nm shift than for SPR based on thin film. This is exemplified with FIG. 26, where the detection of 10 nMIgG is compared for the thin film and for the triangle array. It is observed that the change in SPR response is 5 times larger to the IgG for the triangle array compared to thin film.

These results show that SPR based on various micro structure technologies performs better than current state of the art SPR sensing on thin film.

Although the present invention has been described hereinabove by way of non-restrictive illustrative embodiments thereof, these embodiments can be modified at will within the scope of the appended claims without departing from the spirit and nature of the present invention.

What is claimed is:

1. A method for fabricating a plasmonic structure for use in a surface plasmon resonance sensor, comprising:
   coating a surface of an optically clear substrate with a monolayer of microspheres forming a sphere mask;
   etching the sphere mask to produce an array of microholes;
   depositing an adsorption layer on the etched sphere mask and the surface of the optically clear substrate;
   depositing a metallic film on the adsorption layer; and
   removing the sphere mask.

2. The method of claim 1, further comprising at least one of the following:
   a. etching the sphere mask comprises plasma etching the sphere mask;
   b. coating the surface of the substrate with a solution containing the microspheres;
   c. the substrate is made of an optically clear material selected from the group consisting of glass, silica, silicon, plastic, polymer, and indium tin oxide;
   d. the microspheres have a diameter ranging from 200 nm to 3 µm:
   e. the microspheres comprise polymer microspheres;
   f. the adsorption layer is of a thickness ranging from 0.5 nm to 1 nm;
   g. the adsorption layer is made of material selected from the group consisting of Ti and Cr;
   h. the adsorption layer is deposited using a sputter coater chamber set at a base pressure lower than $1 \times 10^{-4}$ Pa;
   i. the metallic film is of a thickness ranging from 10 nm to 200 nm;
   j. the metallic film is made of a metal selected from the group consisting of gold, silver, copper, platinum, aluminum and palladium;
   k. the metallic film is deposited using a sputter coater;
   l. removing sphere mask comprises immersing the sphere mask in a solvent and applying ultrasounds.

3. The method of claim 1, wherein coating the surface of the substrate is performed with a solution containing the microspheres, and wherein at least one of the following applies;
   a. the solution contains microspheres in suspension with a coefficient of variation lower than 5%;
   b. the solution has a concentration of microspheres by weight of 10%;
   c. the solution contains ethanol and water;
   d. the solution is at room temperature;
   e. the solution is evaporated over a period ranging from one hour to two hours.

4. A surface plasmonic structure for use in a surface plasmon resonance sensor fabricated using the method of claim 1.

5. A surface plasmon resonance sensor, comprising the surface plasmonic structure of claim 4.

6. The method of claim 1, comprising binding a chemically or biologically selective layer to the metallic film to detect corresponding molecules.

7. The method of claim 1, comprising depositing a metal layer on the metallic film to cover the surface of the optically clear substrate at a bottom of the microholes of the array.

8. The method of claim 1, wherein the microspheres have a diameter ranging from 200 nm to 3.2 µm.

9. A surface plasmon resonance sensor, comprising:
   an optically clear substrate prism having a deposition surface;
   an adsorption layer covering the deposition surface; and
   a metallic film deposited on the adsorption layer;
   wherein the adsorption layer and the metallic film comprises an array of microholes.

10. The surface plasmon resonance sensor of claim 9, further comprising:
    a chemically or biologically selective layer bound to the metallic film to detect corresponding, molecules.

11. Use of the surface plasmon resonance sensor of claim 9 for at least one of the following:
    a. tuning a penetration depth of plasmonic structures;
    b. increasing sensitivity to refractive index;
    c. increasing sensitivity to chemical monolayer;
    d. increasing sensitivity to biomolecules;
    e. detecting IgG;
    f. detecting biomolecules selected from the group of proteins, DNA, enzymes, and antibodies;
    g. chemically functionalizing microhole arrays;
    h. tuning an excitation wavelength of surface plasmon resonance in total internal configuration;
    i. for improving detection time of surface plasmon resonance.

12. The surface plasmon resonance sensor of claim 9, wherein the array of microholes has a periodicity ranging from 200 to 10-20 µm.

13. The surface plasmon resonance sensor of claim 9, wherein the adsorption layer has a thickness ranging from 0.5 nm to 5 nm.

14. The surface plasmon resonance sensor of claim 9, wherein the adsorption layer is made of a material selected from the group consisting of Ti and Cr.

15. The surface plasmon resonance sensor of claim 9, wherein the metallic film has a thickness ranging from 10 nm to 200 nm.

16. The surface plasmon resonance sensor of claim 9, wherein the metallic film is made of at least one metal selected from the group consisting of gold, silver, copper, platinum, aluminum and palladium.

17. The surface plasmon resonance sensor of claim 9 further comprising a metal layer covering the deposition surface of the optically clear substrate prism at a bottom of the microholes of the array.

18. The surface plasmon resonance sensor of claim 9, wherein each of the microholes of the array of microholes has a diameter from 200 nm to 3.2 µm.

* * * * *